US00PP33636P2

(12) United States Plant Patent
Lewers et al.

(10) Patent No.: US PP33,636 P2
(45) Date of Patent: Nov. 16, 2021

(54) STRAWBERRY PLANT NAMED 'CORDIAL'

(50) Latin Name: ***Fragaria* x *ananassa* Duchesne ex Rozier**
Varietal Denomination: Cordial

(71) Applicant: The United States of America, as represented by the Secretary of Agriculture, Washington, DC (US)

(72) Inventors: Kimberly S. Lewers, Columbia, MD (US); John M. Enns, Hyattsville, MD (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 16/939,591

(22) Filed: Jul. 27, 2020

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
CPC ... A01H 5/08; A01H 5/02; A01H 6/74; A01H 6/7409
See application file for complete search history.

*Primary Examiner* — June Hwu
(74) *Attorney, Agent, or Firm* — John D. Fado; Mark D. McNemar

(57) ABSTRACT

This invention relates to a new and distinct cultivar of strawberry named 'Cordial'. The new late-season cultivar is primarily characterized by the uniformity and symmetry of fruit shape and size, evenness of color, glossiness of fruit skin, freshness and health of calyx, being free of physiologically-based blemishes such sun scald, bronzing, and rain damage and shelf life of the fruit.

7 Drawing Sheets

Latin name of the genus and species of the plant claimed: 'Cordial' is a new strawberry plant that is *Fragaria* x *ananassa* Duchesne ex Rozier.

Variety denomination: The new strawberry plant claimed is of the variety denominated 'Cordial' *Fragaria* x *ananassa* Duchesne ex Rozier.

BACKGROUND OF THE NEW PLANT

The present invention relates to a new and distinct strawberry cultivar designated 'Cordial' and botanically known as *Fragaria* x *ananassa* Duchesne ex Rozier. This new strawberry cultivar was discovered in Beltsville, Md., in Spring 2013 and originated from a cross between the female parent B1893 (unpatented) and the male parent B1805 (unpatented). The original seedling of the new cultivar was asexually propagated in Beltsville since 2013 by rooting daughter plants from stolons of the mother plant. The present invention has been found to be stable and reproduce true to type through successive asexual propagations rooting daughter plants from stolons.

BRIEF SUMMARY OF THE NEW PLANT

The cultivar 'Cordial' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Cordial'. These characteristics in combination distinguish 'Cordial' as a new and distinct *Fragaria* cultivar:

1. Late season.
2. Resistant to anthracnose fruit rot (*Colletotrichum acutatum*).
3. Excellent fruit quality in storage (shelf life).
4. High yield.

BRIEF DESCRIPTION OF THE PHOTOGRAPHS

This new strawberry plant is illustrated by the accompanying photographs that show the flowers, fruit and entire plants; the colors shown are as true as can be reasonably obtained by conventional photographic procedures.

DETAILED DESCRIPTION OF THE NEW CULTIVAR

Figure 1:
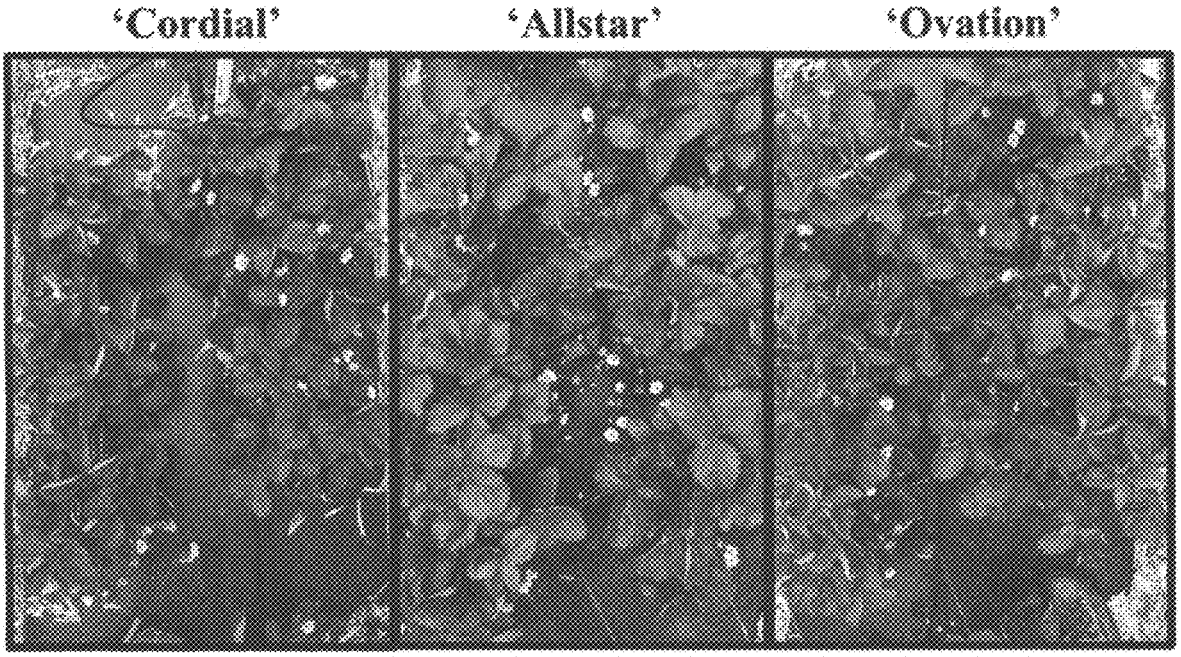
FIG. 1 shows 'Cordial' plant size is smaller than that of 'Ovation' and 'Allstar' while flowering, with 30.5 cm spacing, in annual plasticulture.
Figure 2:
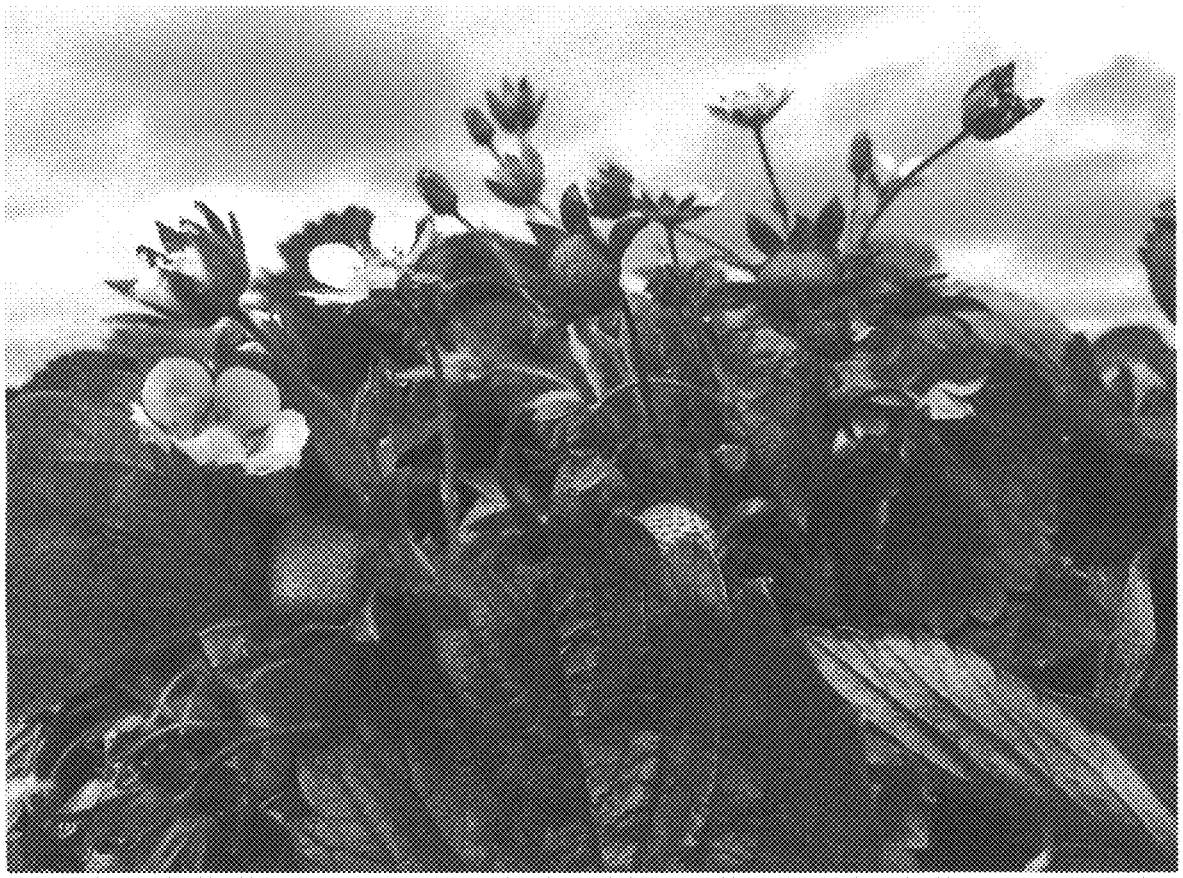
FIG. 2 shows some 'Cordial' terminal flowers are above the canopy, but some are below.
Figure 3:
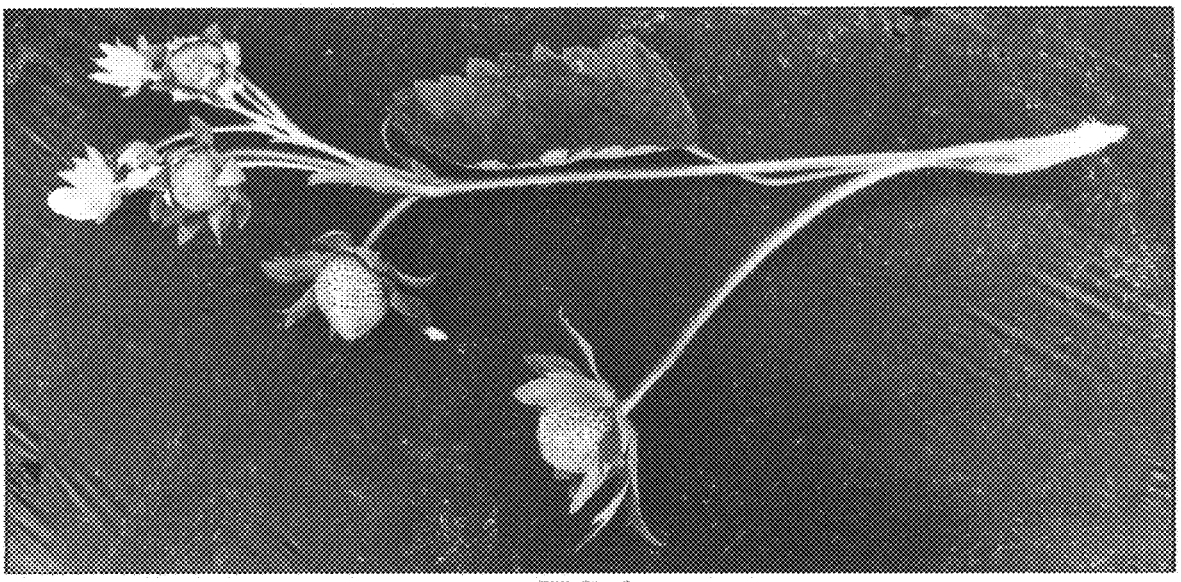
FIG. 3 shows a single 'Cordial' flowering truss.
Figure 4:
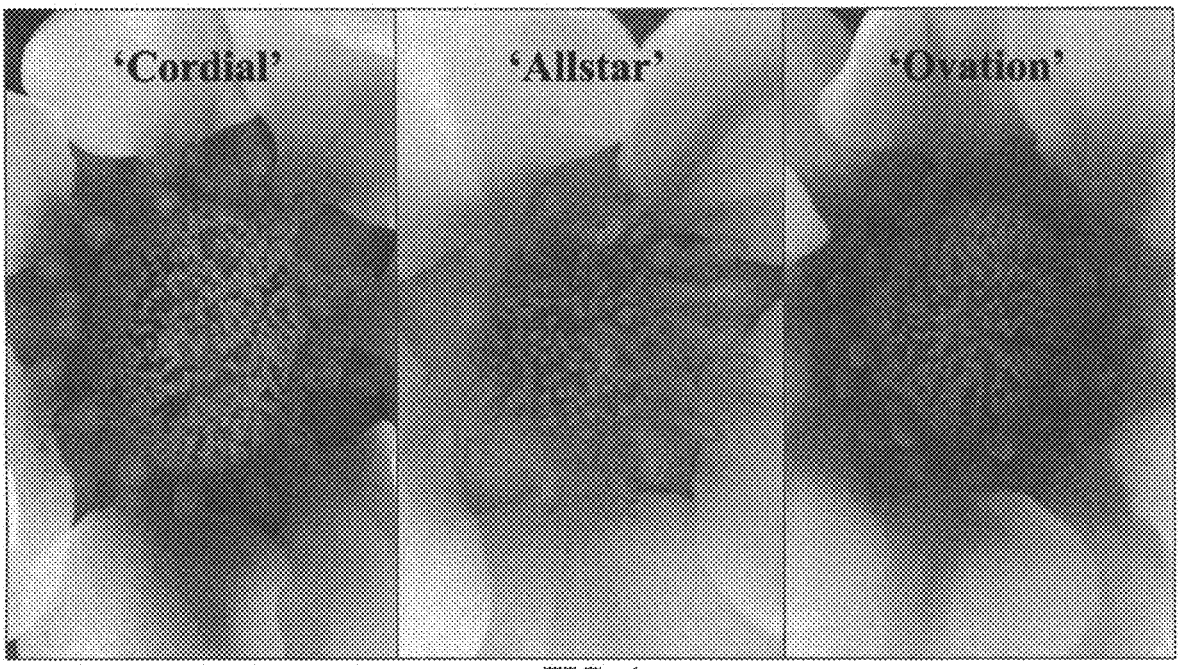
FIG. 4 shows 'Cordial' stigma color is more yellow-orange than that of 'Ovation' and 'Allstar'.
Figure 5:
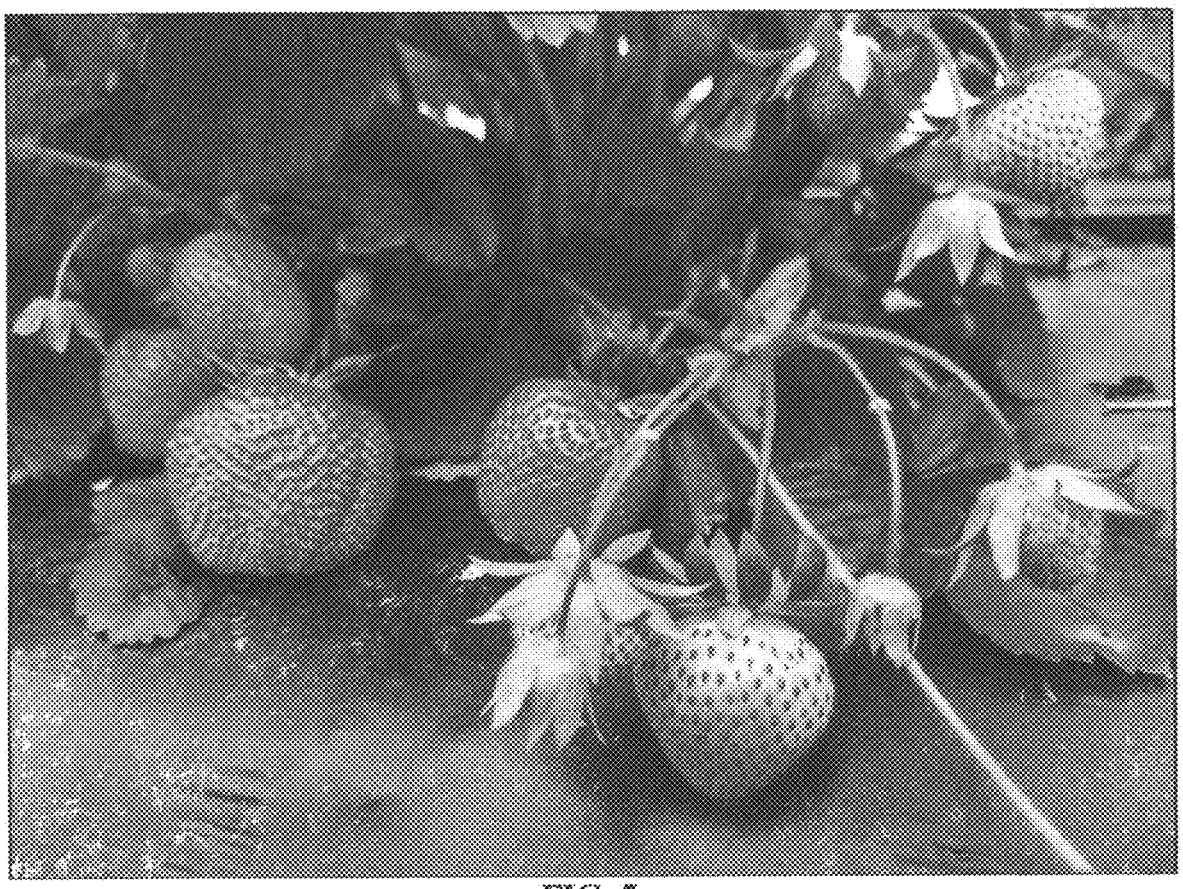
FIG. 5 shows typical 'Cordial' fruit at various ripening stages.
Figure 6:
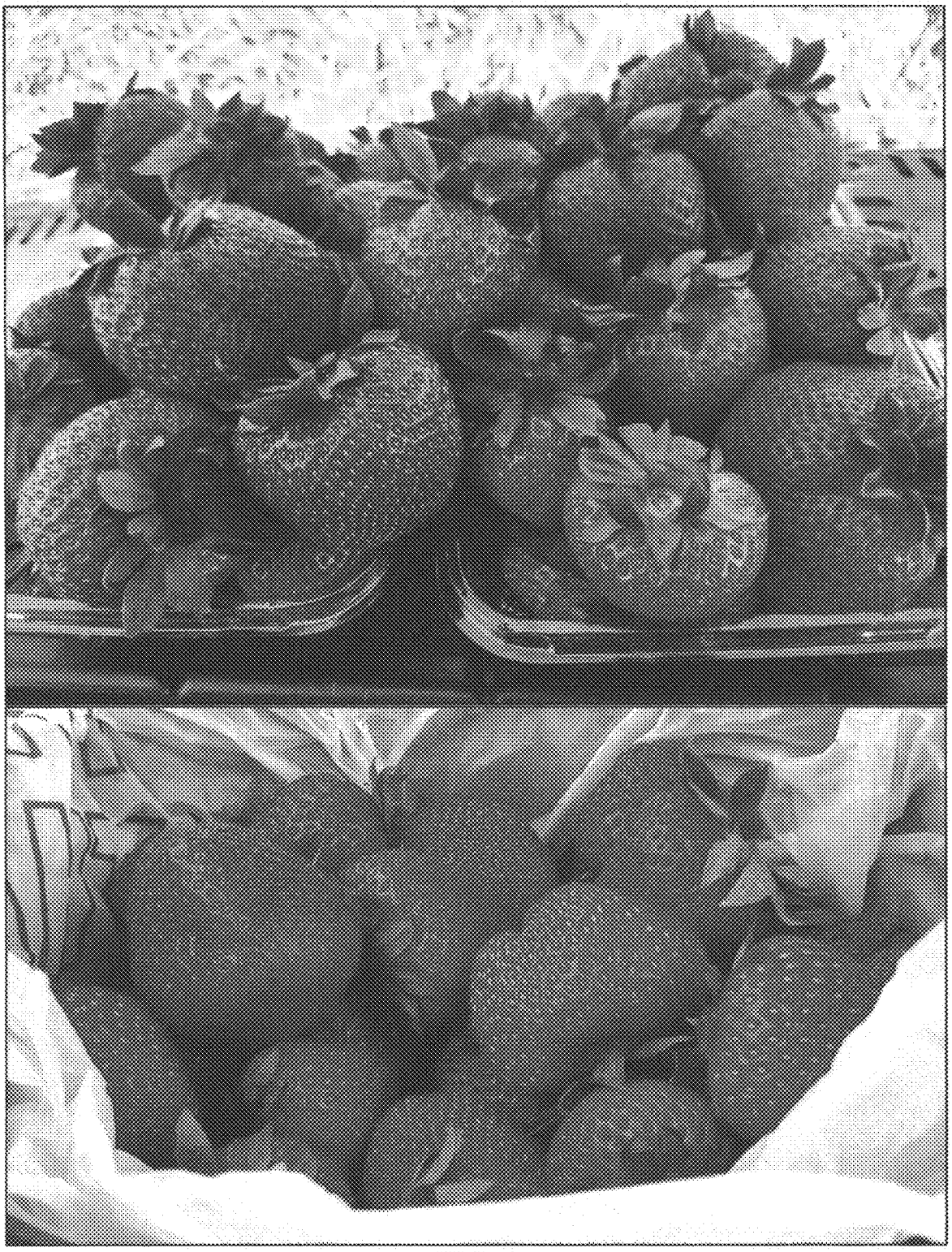
FIG. 6 shows two containers of 'Cordial' fruit photographed two years apart in different outdoor lighting conditions. In one container of fruit on opaque background.
Figure 7:
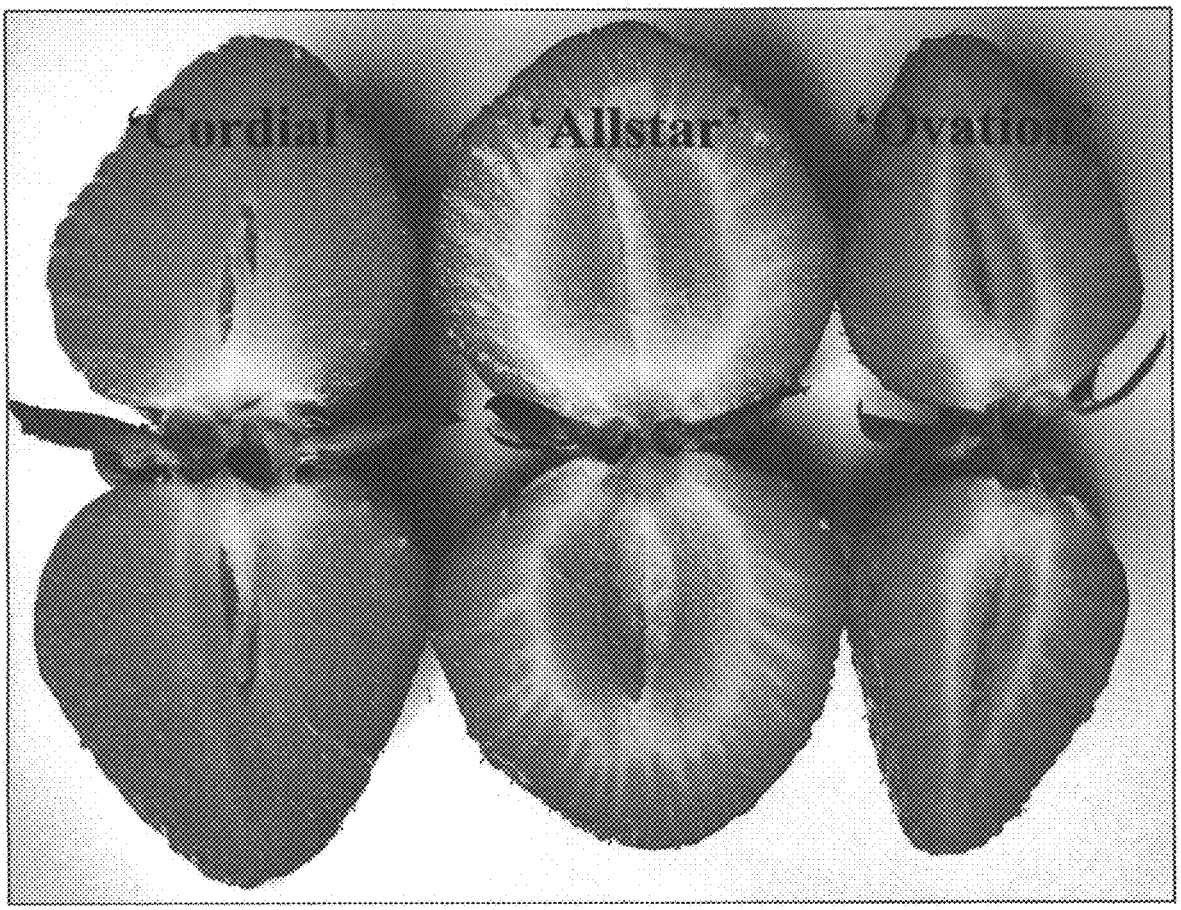
FIG. 7 shows typical halved fruits of 'Cordial' (left), 'Allstar' (center), and 'Ovation' (right), with 'Cordial' flesh having more uniform coloring.

The following description of 'Cordial' is based on observations taken from 2015 through 2018 growing seasons in evaluations in Beltsville, Md. This description is in accordance with UPOV terminology. Color designations, color descriptions, and other phenotypical descriptions may deviate from the stated values and descriptions, depending on variation in environmental, seasonal, climatic, and cultural conditions. 'Cordial' has not been observed under all possible environmental conditions. The botanical description of 'Cordial' was taken from plants nine months after establishment in the field. Color terminology follows The Royal Horticultural Society Colour Chart, London (1986).

'Cordial' fruit are suitable for shipping and fresh-market use, based on a combination of the marketability ratings after refrigerated storage, fruit firmness, and fruit skin toughness. The percent of fruit still at marketable quality (no rot and very little degradation) after refrigerated storage was 86% (1 week) and 52% (2 weeks) for 'Cordial', compared with 37% and 10% for 'Allstar', and 52% and 15% for 'Ovation'.

DETAILED BOTANICAL DESCRIPTION

Table 1 shows selected characteristics of the new cultivar compared with plant characteristics of 'Allstar' and 'Ovation'. Characteristics include inflorescence position, stigma color, anther number, harvest maturity, weight of fruit, yield, firmness of flesh, and evenness of flesh color.

TABLE 1

| Characteristic | 'Cordial' | 'All star' | 'Ovation' |
|---|---|---|---|
| Inflorescence position | Slightly below to above canopy | Slightly below canopy | At or slightly below canopy |
| Stigma color | Yellow-Orange Group 22A | Yellow-Orange Group 22B | Yellow-Orange Group 20B |
| Anther number | 33.2 | 24.6 | 22.2 |
| Harvest maturity (50% of plant with ripe fruit) | Early June | Late May | Early June |
| Weight of fruit (g) | 18.5 | 10.0 | 13.9 |
| Yield (kg/plant) | 0.79 | 0.61 | 0.54 |
| Firmness of flesh | Firm | Medium to firm | Medium to firm |
| Evenness of flesh color | Somewhat even | Not even | Uneven |

Table 2 shows plant characteristics of the new cultivar compared with plant characteristics of 'Allstar' and 'Ovation'. Plant characteristics include plant height, diameter, number of crowns per plant, habit, density of individual plants and vigor.

TABLE 2

| Characteristic | 'Cordial' | 'All star' | 'Ovation' |
|---|---|---|---|
| Plant height (cm) | 27.2 | 31.4 | 28 |
| Plant diameter (cm) | 41.3 | 47.5 | 49.2 |
| Number of crowns plant | 3.8, 3 to 4 | 4.7, 3 to 6 | 4.7, 3 to 7 |
| Habit | Upright open globose | Upright open globose | Upright open globose |
| Density of individual plant | Medium | Medium | Medium |
| Vigor | Medium to strong | Medium | Strong |

Table 3 shows leaf characteristics of the new cultivar compared with leaf characteristics of 'Allstar' and 'Ovation'. Leaf characteristics include leaf type, leaf shape. leaf length, leaf width, terminal leaflet length, terminal leaflet width, terminal leaflet length to width ratio, leaf margins, shape of teeth, leaf serrations per leaflet, upper and lower leaf surface color, number of leaflets, terminal leaflet apex shape, terminal leaflet base shape, glossiness upper side leaf surface, texture upper side leaf surface, texture underside leaf surface and leaf arrangement.

TABLE 3

| Characteristic | 'Cordial' | 'All star' | 'Ovation' |
|---|---|---|---|
| Leaf type | Semi-evergreen | Semi-evergreen | Semi-evergreen |
| Leaf shape | Trifoliolate with ovate leaflets touching to overlapping | Trifoliolate with ovate leaflets touching to overlapping | Trifoliolate with ovate leaflets touching to overlapping |
| Leaf length (cm) | 12.3 | 13.6 | 13.6 |
| Leaf width (cm) | 22.0 | 16.9 | 16.7 |
| Terminal leaflet length (cm) | 10.8 | 9.4 | 9.3 |
| Terminal leaflet width (cm) | 9.4 | 8.2 | 7.8 |
| Terminal leaflet length/width ratio | 1.2 | 1.2 | 1.2 |
| Leaf margins | Serrate | Serrate | Serrate |
| Shape of teeth | Apiculate | Apiculate | Apiculate |
| Leaf serrations per leaflet | 28.6 | 27.3 | 22.7 |
| Color mature leaves lower surface | Green Group 137C | Green Group 137C | Green Group 137C |
| Color mature leaves upper surface | Green Group 137A | Green Group 137A | Green Group 137A |
| Number of leaflets | 3 | 3 | 3 |
| Terminal leaflet apex shape | Obtuse | Obtuse | Obtuse |
| Terminal leaflet base shape | Accute cuneate | Accute cuneate | Accute cuneate |
| Glossiness upper side leaf surface | Semi-gloss | Semi-gloss | Semi-gloss |
| Texture upper side leaf surface | Very slightly rugose | Very slightly rugose | Very slightly rugose |
| Texture underside leaf surface | Very slightly reticulate | Very slightly reticulate | Very slightly reticulate |
| Leaf arrangement | Individual trifoliate leaves attached to compressed stem (crown) at ground level | Individual trifoliate leaves attached to compressed stem (crown) at ground level | Individual trifoliate leaves attached to compressed stem (crown) at ground level |

Table 4 shows information about the petiole, the petiolule, the bract and the stipule of the new cultivar compared to 'Allstar' and 'Ovation'. This includes petiole length, petiole diameter, petiole texture, petiole pubescence, petiole color, petiolule color, petiolule length, bract frequency, bract color designation, stipule length, stipule width, stipule color designation and anthocyanin intensity.

TABLE 4

| Characteristic | 'Cordial' | 'All star' | 'Ovation' |
|---|---|---|---|
| Leaf petiole length (cm) | 18.0 | 24.2 | 21.0 |
| Petiole diameter (cm) | 0.5 | 0.5 | 0.4 |
| Petiole texture | Smooth | Smooth | Smooth |
| Petiole pubescence | Medium | Sparse | Sparse |
| Petiole color | Yellow Green Group 144B | Yellow Green Group 144C with some anthocyanin | Yellow Green Group 144B |
| Petiolule color | Yellow Green Group 144B | Yellow Green Group 144C | Yellow Green Group 144B |
| Petiolule length (cm) | 0.4 | 0.8 | 0.4 |
| Bract frequency | 2 per inflorescence, generally unifoliate | 2 per inflorescence, generally unifoliate | 1 to 2 per inflorescence, generally unifoliate |
| Bract color | Yellow-Green 147A | Yellow-Green 147A | Yellow-Green 147B |
| Stipule length (cm) | 2.4 | 2.3 | 1.9 |
| Stipule width (cm) | 0.8 | 0.8 | 0.6 |
| Stipule color | Absent to very weak | Very weak to weak | Medium |
| Anthocyanin intensity | Red 46B over Yellow-Green 144C | Red 46B over Yellow-Green 144C | Red 46B over Yellow-Green 144C |

Table 5 shows stolon characteristics of the new cultivar compared to 'Allstar' and 'Ovation'. These characteristics include the number of stolons, the anthocyanin coloration of the stolons, the thickness of the stolons, and the pubescence of the stolons.

TABLE 5

| Characteristic | 'Cordial' | 'All star' | 'Ovation' |
|---|---|---|---|
| Stolon production | 9 | 10 | 11 |
| Stolon anthocyanin | Medium | Light | Medium |
| Stolon thickness (cm) | 0.3 | 0.3 | 0.2 |
| Stolon pubescence | Sparse to medium | Sparse | Sparse to medium |

Table 6 shows inflorescence characteristics of the new cultivar compared to 'Allstar' and 'Ovation'. These characteristics include inflorescence position relative to foliage, flower type, flower size, petal shape, relative petal spacing, petal apex shape, petal margin, petal base shape, petal length, petal width, petal length/width ratio, number of petals, petal color, stigma color, style color, anther color, filament color, flower truss type, and anther number.

TABLE 6

| Characteristic | 'Cordial' | 'All star' | 'Ovation' |
|---|---|---|---|
| Inflorescence position | Slightly below to slightly above canopy | Slightly below canopy | At or slightly below canopy |
| Flower type | Complete simple | Complete simple | Complete simple |
| Flower diameter (cm) | 3.6 | 3.7 | 3.4 |
| Petal shape | Circular to obovate | Circular to obovate | Circular to obovate |

TABLE 6-continued

| Characteristic | 'Cordial' | 'All star' | 'Ovation' |
|---|---|---|---|
| Petal spacing | Touching to overlapping | Touching to overlapping | Overlapping |
| Petal apex shape | Circular | Circular | Circular |
| Petal margin | Entire | Entire | Entire |
| Petal base shape | Obovate | Obovate | Obovate |
| Petal length (cm) | 13.0 | 13.0 | 12.7 |
| Petal width (cm) | 11.6 | 12.5 | 12.2 |
| Petal length/width ratio | 1.13 | 1.04 | 1.00 |
| Petal count | 8.0 | 7.2 | 7.2 |
| Petal color | White Group 155D | White Group 155D | White Group 155D |
| Stigma color | Yellow-Orange Group 22A | Yellow-Orange Group 22B | Yellow-Orange Group 20B |
| Style color | Yellow-Green Group 150A | Yellow-Green Group 150B | Yellow-Green Group 150A |
| Anther color | Yellow-Orange Group 20A | Yellow-Orange Group 20A | Yellow-Orange Group 20A |
| Filament color | Yellow-Green Group 150C | Yellow-Green Group 150D | Yellow-Green Group 150D |
| Blooming habit | Spring bloomer | Spring bloomer | Spring bloomer |
| Anther number | 33.2 | 24.6 | 22.2 |

Table 7 shows fruit characteristics of the new cultivar compared to 'Allstar' and 'Ovation'. These characteristics include number of berries per truss, fruiting truss attitude, fruit length, fruit diameter, fruit length/width ratio, fruit weight, relative fruit size, predominant fruit shape, difference in shape between primary and secondary fruit, fruit glossiness, fruit core color, fruit cavity size, band without achenes, evenness of fruit surface, top color, non-blush side color, blush side color, internal color, achene color, achene count per fruit, calyx color, insertion of calyx, pose of calyx segments, size of calyx in relation to fruit, ease of calyx removal, firmness of flesh, evenness of flesh color, distribution of flesh color, sweetness, acidity, Brix, pH, titratable acidity, texture when tasted, time of flowering, harvest maturity (50% of plants with ripe fruit), type of bearing, and yield.

TABLE 7

| Characteristic | 'Cordial' | 'All star' | 'Ovation' |
|---|---|---|---|
| Number of berries per fruiting truss | 9.2 | 11.3 | 13.5 |
| Fruiting truss attitude | Prostrate | Prostrate | Prostrate |
| Diameter fruit (cm) | 4.8 | 4.3 | 3.5 |
| Length fruit (cm) | 4.2 | 4.3 | 4.2 |
| Ratio fruit length/width | 0.9 | 1.0 | 1.2 |
| Weight of fruit (g) | 18.5 | 10.0 | 13.9 |
| Relative fruit size | Medium to Large | Medium | Medium to Large |
| Predominant fruit shape | Conic to globose conic | Conic | Conic |
| Difference in shap ebetween primary and secondary fruits | Slight, more uniform | Moderate | Moderate |
| Fruit glossiness | Strong | Strong | Strong |
| Fruit core color | Light red | Light red | Light red |
| Fruit cavity size | Absent to small | Absent to small | Absent to small |
| Band without achenes | Absent to very narrow | Absent to moderate | Absent to moderate |
| Evenness of | Very even | Even to slightly | Even to slightly |

TABLE 7-continued

| Characteristic | 'Cordial' | 'All star' | 'Ovation' |
|---|---|---|---|
| fruit surface | | uneven | uneven |
| Color of top of fruit | Red Group 45A | Red Group 44A | Red Group 45A |
| Non-blush side color | Red Group 44A | Orange-Red Group 33A | Red Group 44A |
| Blush side color | Red Group 45A | Red Group 45A | Red Group 45A |
| Internal flesh color | Orange-Red Group 33A 33B, White 155D | Orange-Red Group 33A 33B 33C, Orange-White Group 159D | Orange-Red Group 33A 33B, White 155D |
| Achene position | At surface | At surface | At surface |
| Achene color | Yellow-Green Group 153B, Red Group 45A | Greyed-Yellow Group 160A, Red Group 45A | Greyed-Yellow Group 160B, Red Group 45A |
| Achene count | 519 | 397 | 248 |
| Insertion of calyx | At surface | At surface slightly necked | At surface to slightly necked |
| Calyx color | Yellow-Green 148B | Yellow-Green 148B | Yellow-Green 148B |
| Pose of calyx segments | Reflexed to spreading | Reflexed to clasping | Reflexed to spreading |
| Size of calyx in relation to fruit | Same to larger | Same to slightly larger | Slightly smaller to slightly larger |
| Ease of calyx removal | Difficult | Difficult | Difficult |
| Firmness of flesh | Firm | Medium to firm | Medium to firm |
| Evenness of flesh color | Somewhat even | Not even | Uneven |
| Distribution of flesh color | Orange-red heart, slightly darker exterior, white near the proximal end | Relatively large light orange-red heart, very pale ring and lines radiating to achenes, orange red exterior, | Orange-red heart, white ring, orange red exterior, with visible lines towards each achene |
| Sweetness | Medium | Medium | Medium |
| Acidity | Mild | Mild | Mild |

TABLE 7-continued

| Characteristic | 'Cordial' | 'All star' | 'Ovation' |
|---|---|---|---|
| Brix (percent soluble solids) | 7.6 | 7.5 | 7.8 |
| pH | 3.79 | 3.85 | 3.55 |
| Texture when tasted | Fine and juicy | Fine and juicy | Fine and juicy |
| Time of flowering | April to May | April to May | April to May |
| Harvest maturity (50% of plant with ripe fruit) | Early June | Late May | Early June |
| Type of bearing | Short Day/June Bearing | Short Day/June Bearing | Short Day/June Bearing |
| Yield (kg/plant) | 0.79 | 0.61 | 0.54 |

COMPARISON WITH PARENTAL AND OTHER CULTIVARS

When 'Cordial' is compared to female parent, B1893 (unpatented), the fruits are less susceptible to *Botrytis* fruit rot (*Botrytis cinerea*). When 'Cordial' is compared to male parent, B1805 (unpatented), a full sibling of 'Keepsake' (U.S. Plant Pat. No. 30,578), the fruits are more resistant to anthracnose fruit rot (*Colletotrichum acutatum*) and produce more stolons (runners). 'Cordial' plants respond to powdery mildew (*Spaerotheca macularis*), leaf blight (*Phomopsis obscurans*), leaf scorch (*Diplocarpon earliana*), and common leaf spot (*Mycosphaerella fragariae*) similarly to those of 'Allstar' and are less susceptible than 'Ovation' plants. 'Cordial' plants respond to bacterial angular leafspot (*Xanthomonas fragariae*) similarly to those of 'Ovation' and are less susceptible than 'Allstar' plants.

We claim:

1. A new and distinct cultivar of strawberry plant named 'Cordial', substantially as illustrated and described herein.

* * * * *